(12) United States Patent  (10) Patent No.: US 7,850,644 B2
Gonzalez et al.  (45) Date of Patent: *Dec. 14, 2010

(54) FLEXIBLE POLYMER NEEDLE CATHETER

(75) Inventors: Fernando Gonzalez, Campbell, CA (US); William E. Webler, Escondido, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1613 days.

This patent is subject to a terminal disclaimer.

(21) Appl. No.: 11/031,608

(22) Filed: Jan. 5, 2005

(65) Prior Publication Data

US 2005/0124977 A1  Jun. 9, 2005

Related U.S. Application Data

(62) Division of application No. 10/263,640, filed on Oct. 2, 2002, now Pat. No. 6,855,124.

(51) Int. Cl.
A61M 29/00 (2006.01)
(52) U.S. Cl. .............. 604/96.01; 604/164.12; 604/272; 604/523; 604/525; 604/526; 604/527; 604/533; 604/534; 604/535
(58) Field of Classification Search ......... 604/272, 604/523, 525, 526, 527, 533, 534, 535, 545, 604/96.01, 164.1
See application file for complete search history.

(56) References Cited

U.S. PATENT DOCUMENTS

| | | | | |
|---|---|---|---|---|
| 2,512,569 A | * | 6/1950 | Saffir | 604/272 |
| 3,584,624 A | * | 6/1971 | de Ciutiis | 604/170.01 |
| 3,780,733 A | * | 12/1973 | Martinez-Manzor | 604/158 |
| 3,890,976 A | * | 6/1975 | Bazell et al. | 128/207.15 |
| 4,842,590 A | * | 6/1989 | Tanabe et al. | 604/524 |
| 5,092,848 A | * | 3/1992 | deCiutiis | 604/170.01 |
| 5,336,252 A | | 8/1994 | Cohen | |
| 5,354,279 A | | 10/1994 | Hofling | |
| 5,380,292 A | | 1/1995 | Wilson | |
| 5,437,632 A | | 8/1995 | Engelson | |
| 5,464,395 A | * | 11/1995 | Faxon et al. | 604/103.02 |
| 5,499,630 A | * | 3/1996 | Hiki et al. | 600/461 |
| 5,730,732 A | * | 3/1998 | Sardelis et al. | 604/272 |

(Continued)

FOREIGN PATENT DOCUMENTS

EP  0861632 A1  9/1998

(Continued)

OTHER PUBLICATIONS

PCT International Search Report for PCT Appln No. US03/30464, mailed Feb. 9, 2004 (7 pages).

*Primary Examiner*—Nicholas D Lucchesi
*Assistant Examiner*—Scott Medway
(74) *Attorney, Agent, or Firm*—Blakely Sokoloff Taylor & Zafman LLP

(57) ABSTRACT

A catheter device having an elongated tubular member with a proximal end and a distal end, and a needle disposed near the distal end. In one embodiment, the needle has a rigid, penetrating tip coupled to a flexible portion by an overlapping joint. The flexible portion enables the needle to bend to a penetrating angle relative to the distal end of the elongated tubular member and penetrate a body tissue without kinking.

30 Claims, 9 Drawing Sheets

U.S. PATENT DOCUMENTS

| | | | |
|---|---|---|---|
| 5,785,689 A | 7/1998 | De Toledo et al. | |
| 6,093,177 A | 7/2000 | Javier, Jr. et al. | |
| 6,162,202 A * | 12/2000 | Sicurelli et al. | 604/272 |
| 6,183,444 B1 | 2/2001 | Glines et al. | |
| 6,190,353 B1 * | 2/2001 | Makower et al. | 604/95.01 |
| 6,206,893 B1 | 3/2001 | Klein et al. | |
| 6,241,710 B1 | 6/2001 | VanTassel et al. | |
| 6,283,947 B1 * | 9/2001 | Mirzaee | 604/264 |
| 6,358,258 B1 | 3/2002 | Arcia et al. | |
| 6,494,862 B1 * | 12/2002 | Ray et al. | 604/96.01 |
| 6,544,230 B1 * | 4/2003 | Flaherty et al. | 604/164.12 |
| 6,599,267 B1 | 7/2003 | Ray et al. | |
| 6,692,466 B1 * | 2/2004 | Chow et al. | 604/164.01 |
| 6,926,692 B2 * | 8/2005 | Katoh et al. | 604/164.01 |
| 7,008,411 B1 * | 3/2006 | Mandrusov et al. | 604/506 |
| 7,035,092 B2 * | 4/2006 | Hillman et al. | 361/683 |
| 7,438,692 B2 * | 10/2008 | Tsonton et al. | 600/564 |
| 2001/0023349 A1 | 9/2001 | VanTassel et al. | |

FOREIGN PATENT DOCUMENTS

| | | |
|---|---|---|
| EP | 0938871 A2 | 9/1999 |
| WO | WO-9210142 | 6/1992 |
| WO | WO 00/71196 A1 | 11/2000 |
| WO | WO 01/45548 A2 | 6/2001 |
| WO | WO 01/49357 A2 | 7/2001 |

* cited by examiner

A - A

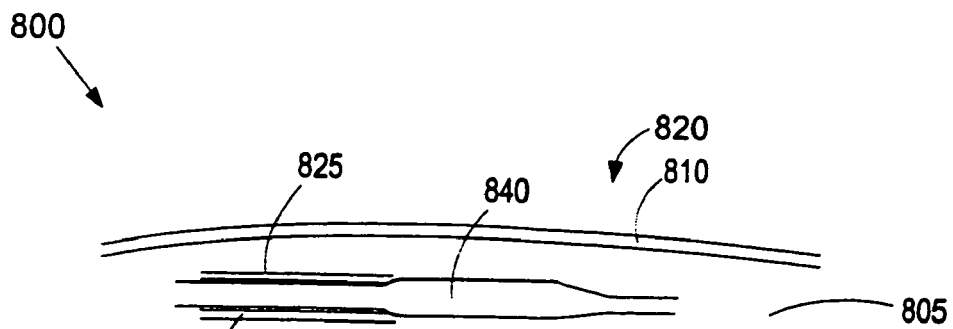
FIG. 8A
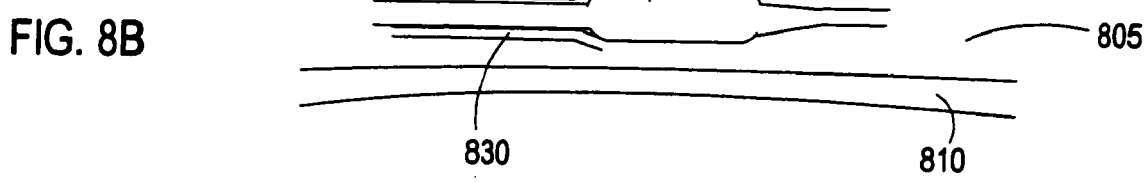
FIG. 8B
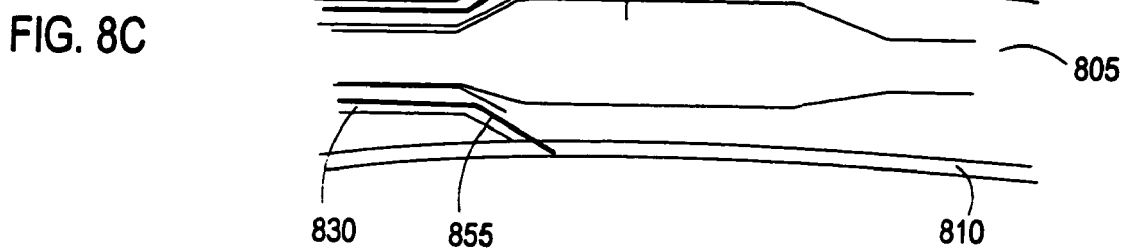
FIG. 8C
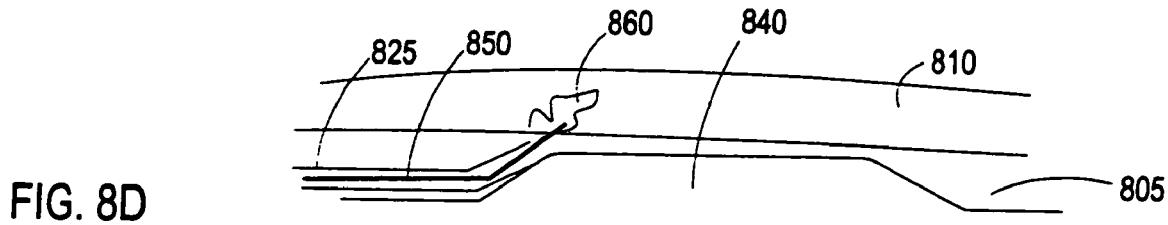
FIG. 8D
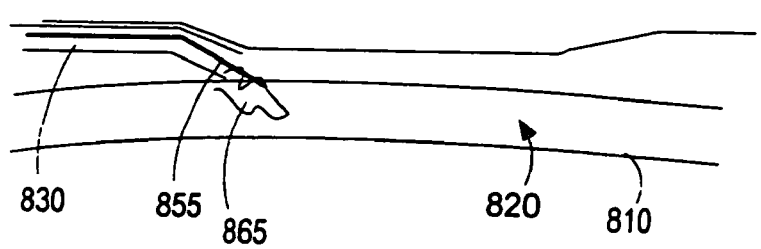

FLEXIBLE POLYMER NEEDLE CATHETER

This application is a divisional application of U.S. patent application Ser. No. 10/263,640, filed Oct. 2, 2002 now U.S. Pat. No. 6,855,124.

FIELD OF THE INVENTION

The invention, in one embodiment, relates generally to catheters, and more particularly, in one embodiment, to percutaneous needle catheters.

BACKGROUND OF THE INVENTION

Atherosclerosis, a process in which the walls of the arteries thicken due to the accumulation of plaque in the blood vessels, is the cause of most coronary artery disease (CAD) that can result in heart attacks, strokes, or inadequate circulation to the extremities. Arterial occlusions caused by plaque accumulation may necessitate major invasive surgery, such as a coronary by-pass procedure. However, less invasive, percutaneous methods may be an alternative in treating atherosclerosis. For example, percutaneous transluminal coronary angioplasty (PTCA) involves advancing a balloon catheter through a body lumen to a target treatment site. In one example, a small incision is made near the femoral artery to insert the catheter, which is then advanced to a plaque area in the coronary artery. The catheter has a deflated balloon near a distal end, and the balloon is positioned across the plaque. Once in position, the balloon is inflated to crack or flatten the plaque, thereby restoring the normal patency of the blood vessel. The balloon is then deflated so that the catheter can be removed, allowing blood flow to resume through the dilated blood vessel.

Percutaneous delivery of therapeutic agents may also be performed alone or in combination with PCTA treatments. Needle catheters are one type of percutaneous medical devices that may be used to deliver a therapeutic agent or drug to treat diseases associated with CAD. However, the tortuous nature of vessels in the body make it difficult for advancing a needle catheter to a target treatment site. Furthermore, to optimize a therapeutic drug treatment, the active drug or biologic agent may need to be injected directly into a vessel wall. This type of drug delivery requires a high level of accuracy because the proper point in the vessel wall should be penetrated. In another type of drug delivery treatment with a needle catheter, biologically active agents may be delivered to a cardiac structure (such as into an intraventricular wall), which also requires that the needle catheter be flexible enough to navigate and advance through body vessels and to the heart. U.S. Pat. No. 6,093,177 describes one type of flexible catheter that may be used within a heart chamber.

FIG. 1 illustrates an example of a prior art needle catheter. The needle tip is connected to a needle shaft that may be steered and moved from a retracted position within a sleeve and an extended position past a distal end of the sleeve to penetrate a body tissue. The needle shaft may have a tubular lumen so that a drug or biologic agent may be injected through the needle tip to the body tissue. The needle tip (along with the needle shaft) is usually a continuous piece of metallic material to provide sufficient strength and support to prevent kinking during advancement through a tortuous vessel and tissue penetration.

One problem with a metallic needle and/or needle shaft is that it may not provide the necessary flexibility to navigate through tortuous body vessels, which are characteristic of arterial regions. Because of the lack of flexibility of these needle catheters, it may be difficult to deliver biologic agents deep within the arterial regions of the body. Moreover, it may be even more difficult to bend the penetrating tip of the needle to pierce a vessel wall to optimize drug delivery treatment.

SUMMARY OF THE INVENTION

A catheter device having an elongated tubular member with a proximal end and a distal end, and a needle disposed near the distal end is described. In one embodiment, the needle has a rigid, penetrating tip coupled to a flexible portion by an overlapping joint. The flexible portion enables the needle to bend to a penetrating angle relative to the distal end of the elongated tubular member and penetrate a body tissue without kinking.

BRIEF DESCRIPTION OF THE DRAWINGS

The present invention is illustrated by way of example, and not limitation, in the figures of the accompanying drawings in which:

FIGS. 8A-8D illustrate an exemplary method of delivering a biologic agent to a body tissue using a flexible needle catheter.

DETAILED DESCRIPTION

In the following description, numerous specific details are set forth such as examples of specific, components, processes, etc. in order to provide a thorough understanding of various embodiment of the present invention. It will be apparent, however, to one skilled in the art that these specific details need not be employed to practice various embodiments of the present invention. In other instances, well known components or methods have not been described in detail in order to avoid unnecessarily obscuring various embodiments of the present invention. The term "coupled" as used herein means connected directly or indirectly through one or more intervening structures or elements.

Various embodiments of a flexible needle catheter and methods for using a needle catheter are described. The needle catheter, in one embodiment, may be used to delivery a bioactive agent or therapeutic drug percutaneously by advancing the needle to a target treatment region (e.g., an arterial wall or within a cardiac chamber). As used herein, the terms "bioactive agent," "therapeutic agent," or "therapeutic drug" are used interchangeably to refer to substances that are known to one skilled in the art to treat various types of diseases or ailments. These substances may take the form of fluids, solids (e.g., microcapsules) or any other form that may be injected with a needle catheter.

In one embodiment, the needle of the needle catheter may have a rigid, penetrating tip coupled to flexible portion by a first overlapping joint. The penetrating tip of the needle may be a metallic material such as stainless steel. The flexible portion of the needle may be a polymer or polymer blend to enable the needle to bend to a penetrating angle relative to the distal end of the catheter so that the penetrating tip may pierce a body tissue without kinking. In another embodiment, the flexible portion of the needle may be coupled to a needle shaft by a second overlapping joint. The needle shaft may be may be metallic or polymer based. Alternatively, the flexible portion coupled to the needle tip portion may be reinforced with embedded braided or coiled wire(s) embedded within the walls of the flexible portion.

Figure 1:
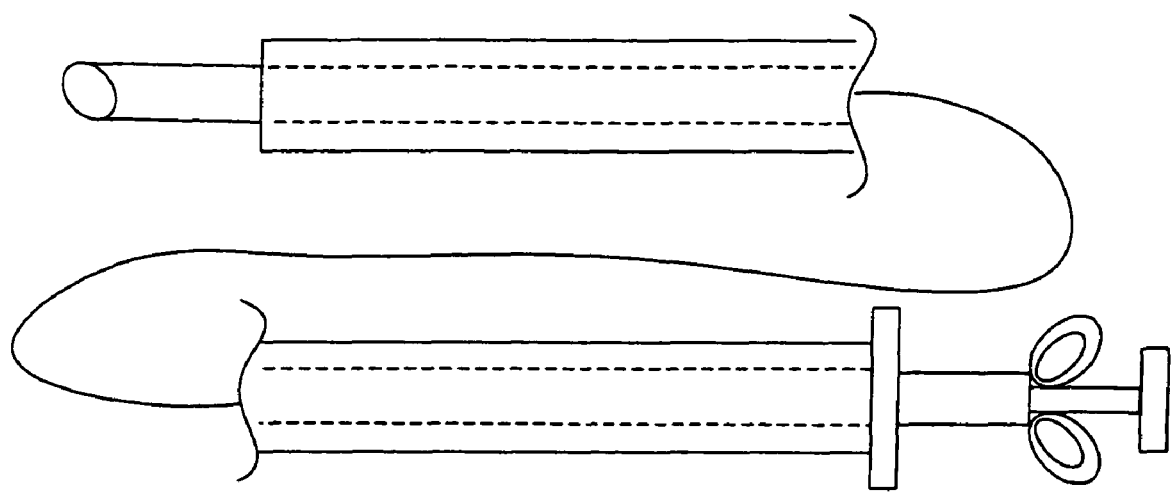
FIG. 1 illustrates a prior art needle catheter.
Figure 2:
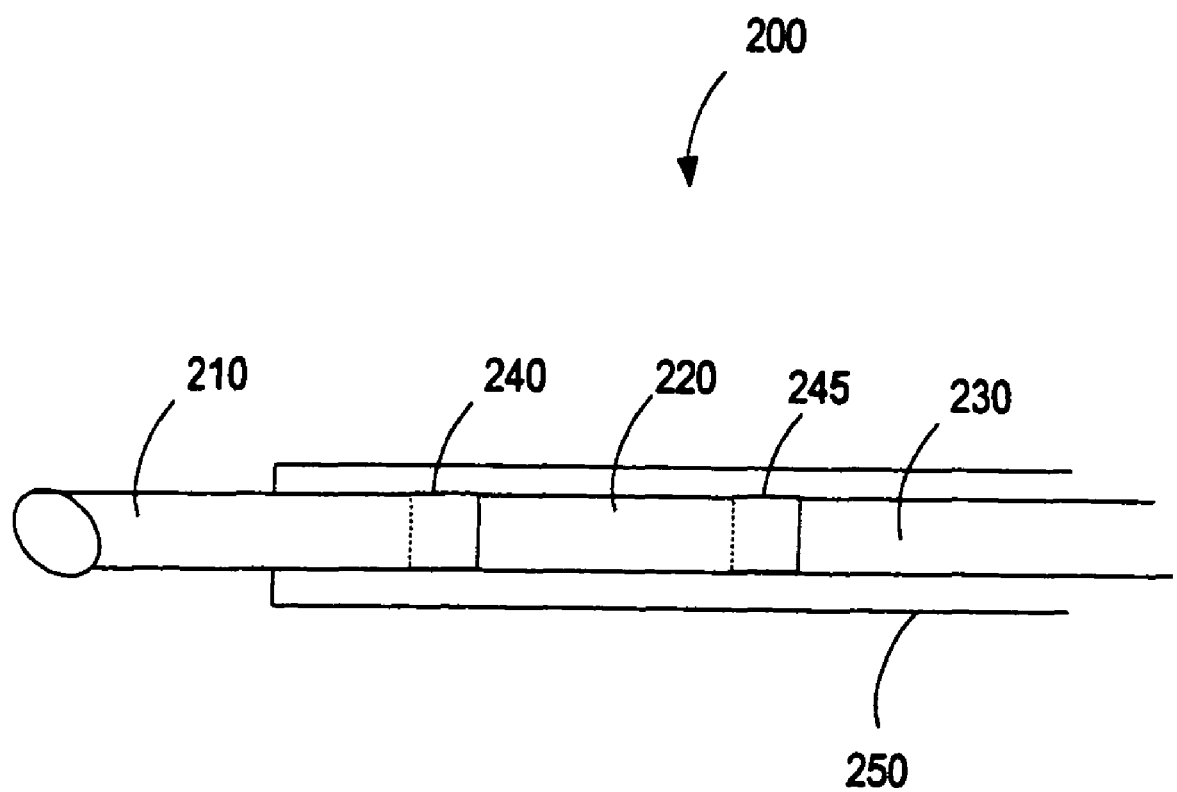
FIG. 2 illustrates an exemplary embodiment of a needle for use with a needle catheter having a rigid tip portion coupled to a flexible portion.

FIG. 2 illustrates one embodiment of a needle of the present invention that may be used in a needle catheter. Needle 200 has tip portion 210, flexible portion 220, needle shaft portion 230, first overlapping joint 240 and second overlapping joint 245. In one embodiment, needle 200 may be part of a needle catheter assembly in which needle 200 may be the disposed near a distal end of the catheter. Needle 200 is illustrated in a partially extended position from sheath 250. In a retracted position (not shown), tip portion 210 would be completely housed within sheath 250. For example, the needle would remain in the retracted position until it has advanced to the target region within a patient's body, just before extending to penetrate a body tissue and inject a biologically active agent into the body tissue (discussed in greater detail with respect to FIGS. 8A-8D).

Needle 200 has tip portion 210, flexible portion 220, and needle shaft portion 230 all coupled together to form one continuous needle structure. In one embodiment, needle 200 may be hollow with a beveled tip portion 210 to penetrate, for example, a body tissue and deliver a biologic agent. Tip portion 210 is coupled to flexible portion 220 by forming a first overlapping joint 240 near a distal end of needle 200. Flexible portion 220 is coupled to needle shaft 230 by forming a second overlapping joint 245 proximal to first overlapping joint 240. The combined tip portion 210 and flexible portion 220 of needle 200 may have a length in a range from 10 to 20 millimeters. In one embodiment, needle 200 has needle tip portion 210 of length 5 millimeters with an inner diameter of 20 mils and an outer diameter of 27 mils. Flexible tubing 220 has a length of 10 millimeters with an inner diameter of 8.7 mils and an outer diameter of 14.2 mils. The length of first and second overlap joints may be between 4-8 millimeters.

Tip portion 210 is made of a material rigid enough to penetrate a body tissue. In one embodiment, tip portion 210 may be a stainless steel tip (SST). In another embodiment, tip portion 210 may be made of comparable metallic material to that of stainless steel known to one of skill in the art, including shape memory alloys (e.g., nickel-titanium, also referred to as "NiTi" or "NiTinol"). In another alternative embodiment, tip portion 210 may be made of ceramic or material which are compatible with MRI (magnetic resonance imaging) in that the materials do not introduce artifacts in MRI images.

Flexible portion 220 enables tip portion 210 of needle 200 to bend to a necessary penetration angle to pierce a target body tissue. Flexible portion 220 may be made of any high modulus/high strength polymer grade or polymer blend. Grade, formulations, or blends of polymers that may be used for flexible member 220 include, but are not limited to polyimide, polyether block amide or polyester block amide (PEBAX), polyetheretherketone (PEEK), polyethylene terephthalate (PET), polybutylene terephthalate (PBT), polyetherimide (PEI), polystyrene (PS), acetel, polymethylmethacrylate (PMMA or acrylic), nylon, Teflon, and polyvinyl chloride (PVC). Some of the factors that may influence the proper material include the dimensions of the flexible portion and the forces, pressures, and deformations that the flexible portion may be subjected to during use. The flexible portion 220, being hollow in one embodiment, may have strength and modulus as the main limitations for determining a suitable flexible material. If the modulus or strength is too low, then the wall may not be able to resist injection pressures (i.e., excessive deformation, compliance or rupture), or be unable to apply enough force to needle tip portion 210 to penetrate a body tissue (i.e., excessive compression or low compression modulus). Flexible portion 220 may also break when subjected to a tortuous environment and/or lack the ability to control needle tip portion 210 to desired penetration angles. Material modulus and strength interact. If the modulus is high enough to satisfy compression and/or compliance issues, then its strength must be proportionally as high to deal with rupture and/or bending issues. These materials disclosed above may also be used to impregnate a spring(s) and/or a braid(s) to form and/or reinforce the shaft. In one embodiment, sheath 250 may also be made of materials comparable to flexible portion 220 because sheath 250 may need to bend and flex with needle 200.

Needle shaft 230, as part of the needle catheter coupled to flexible portion 220 and tip portion 210, should possess flexible properties to advance through a tortuous body lumen while providing sufficient support such that it does not kink or collapse during this advancement or when it is advanced relative to sheath 250 to cause tip portion 210 to penetrate body tissue. As such, needle shaft 230 may be bent during use, particularly near a distal end of needle 200. In one embodiment, needle shaft 230 may be made of polymers or polymer blends discussed above with respect to flexible portion 220 of needle 200 in order to provide similar flexural properties. Alternatively, needle shaft 230 may be made of metallic or ceramic materials discussed above with respect to tip portion 210 of needle 200.

Shaft 230 is also flexible to limit the friction forces between it and sheath 250 when in a tortuous anatomy. If shaft 230 is not flexible enough, then the forces during needle 200 advancement (relative to sheath 250) could stretch the catheter, shear/peal sheath 250 away from the catheter, break catheter/sheath bonds, compress the shaft (retarding penetration) or make it very difficult to advance (cause penetration), as well as, retract. During retraction similar problems may occur, except the catheter/sheath bonds may be compressed.

Figure 3A:
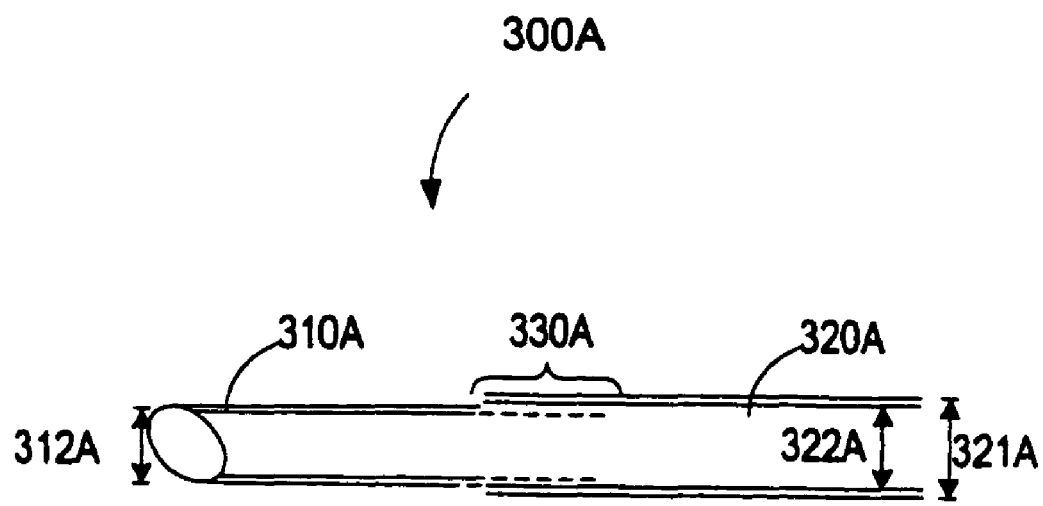
FIG. 3A illustrates an exemplary embodiment of an overlapping joint of a needle for use with a needle catheter.
Figure 3B:
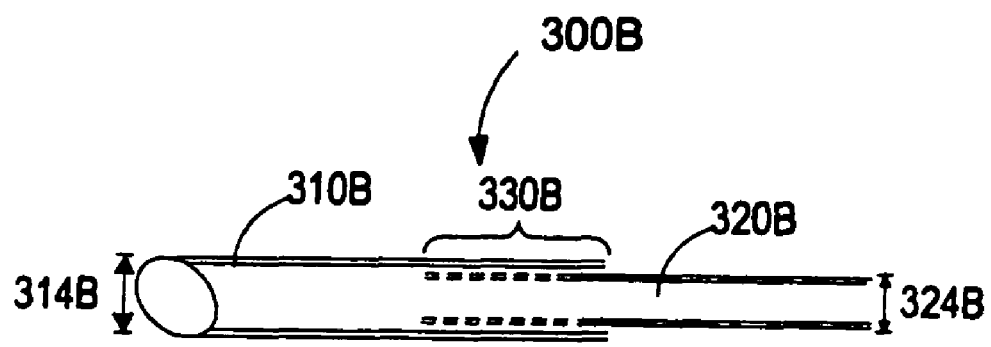
FIG. 3B illustrates another exemplary embodiment of an overlapping joint of a needle for use with a needle catheter.

As noted above, tip portion 210 is coupled to flexible portion 220 by forming a first overlapping joint 240. FIG. 3A and FIG. 3B illustrate needles 300A and 300B having embodiments of overlapping joint structures 330A and 330B between tip portions 310A, 310B and flexible portions 320A, 320B. For clarity of description, needles 300A and 300B are illustrated without a sheath or needle shaft coupled to flexible portions 320A, 320B. FIG. 3A illustrates overlap joint 330A formed by flexible portion 320A overlapping tip portion 310A. Outer diameter (OD) 312A of tip portion 310A is smaller than inner diameter (ID) 322A (and also outer diameter 321A) of flexible portion 320A of overlap joint 330A. Alternatively, OD 312A of tip portion 310A may be substantially similar to ID 322A of tip portion near a distal end of tip portion 310A but tapers to a smaller OD near flexible portion 320A so as to fit inside of flexible portion 320A. In one embodiment, the two portions may be bonded together with an adhesive (e.g., Loctite 4061). Comparable adhesives known in the art may also be used to bond tip portion 310A to flexible portion 320A to form overlap joint 330A. In one embodiment, overlap joint 330A may have a length of about 0.5 millimeters to provide sufficient bonding area between tip portion 310A and flexible portion 320A.

Alternatively, overlapping joint 330B may perform better when the bonding positions are reversed. As illustrated by FIG. 3B, flexible portion 320B is placed inside tip portion 310B such that an outer diameter 324B of flexible portion 320B is inside an inner diameter 314B of tip portion 314B. Flexible portion 320B may have the lowest modulus or change its dimensions more in response to pressure on the ID when a drug is injected through flexible portion 320B, thereby subjecting overlap joint 330B to a peel-type force that would separate tip portion 310B from flexible portion 320B. In other words, flexible portion 320B may expand more and have a tendency to separate from tip portion 310B. If flexible portion 320B, made from a polymer or polymer blend as discussed above, is overlapped by tip portion 310B, the expansion flexible portion 320B at joint 330B, may be limited by the stiffer tip portion and the forces generated may have a tendency to seal overlap joint 330B, rather than peel it apart. This may produce a more reliable, leak-proof joint 330B.

Figure 4A:
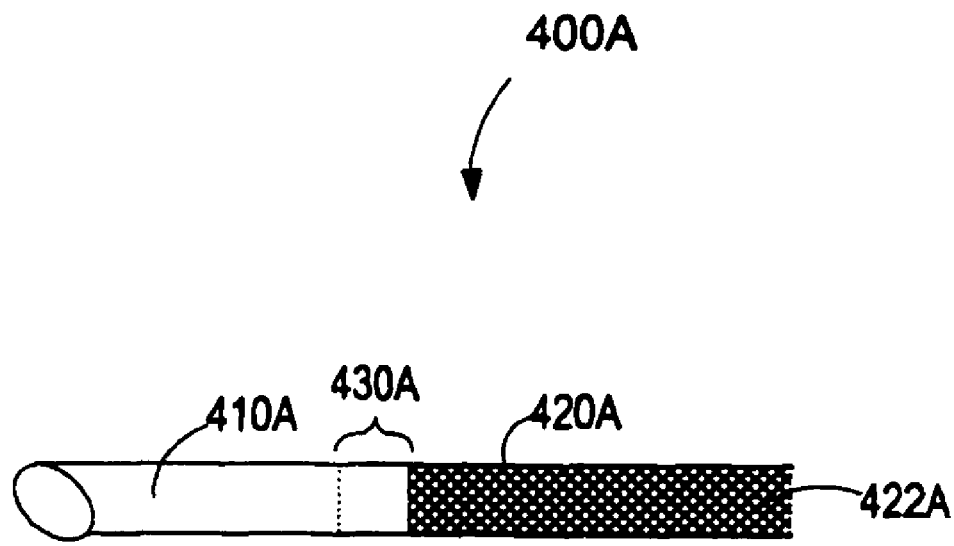
FIG. 4A illustrates an exemplary embodiment of a flexible portion of a needle reinforced with braided wire for use with a needle catheter.
Figure 4B:
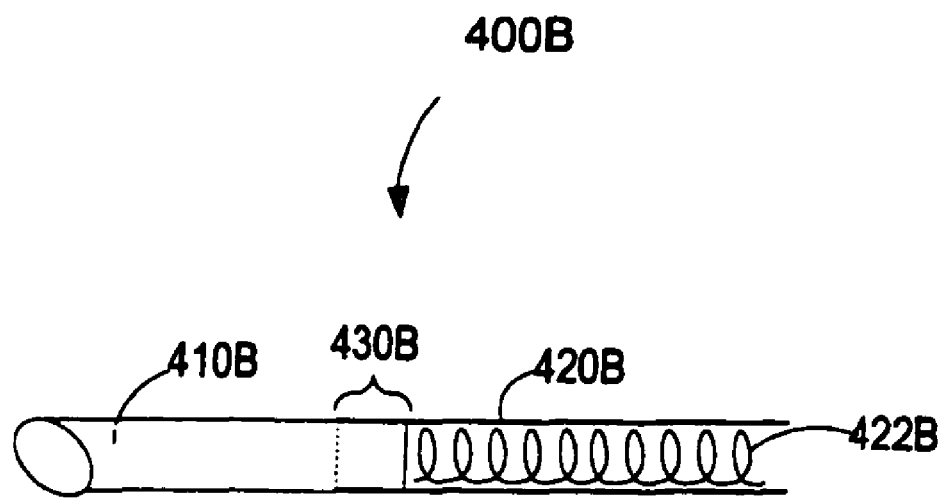
FIG. 4B illustrates another exemplary embodiment of a flexible portion of a needle reinforced with wire coil for use with a needle catheter.

In one embodiment, in addition to the various polymers and polymer blends discussed above with respect to materials that may be used for the flexible portion of a needle, flexible portions 320A, 320B may be reinforced with additional elements to exhibit suitable modulus and/or strength properties. Dimensions being equal, a polymer flexible portion may compress or elongate more than a metallic portion under the same forces, thereby raising issues of needle longitudinal position control with a polymer flexible portion and/or needle shaft. This may be mitigated by the use of braids or springs within the polymer wall. Moreover, reinforcing flexible portions 320A, 320B increases their resistance to kinking or buckling (i.e., compressive failure), events that may compromise injection capability. FIGS. 4A and 4B illustrate flexible portions 420A and 420B and needle tip portions 410A and 410B of needles 400A and 400B embedded with reinforcing elements 422A and 424B, respectively. In another embodiment, the reinforcing elements may extend to the needle shaft (e.g., needle shaft 230 of FIG. 2). FIG. 4A illustrates flexible portion 420A (e.g., made of a polymer or polymer blend) reinforced with very thin wire in a braided pattern 422A. Alternatively, FIG. 4B illustrates flexible portion 420B of need 400B reinforced with very thin wire in a coil or spring pattern 422B.

Figure 5:
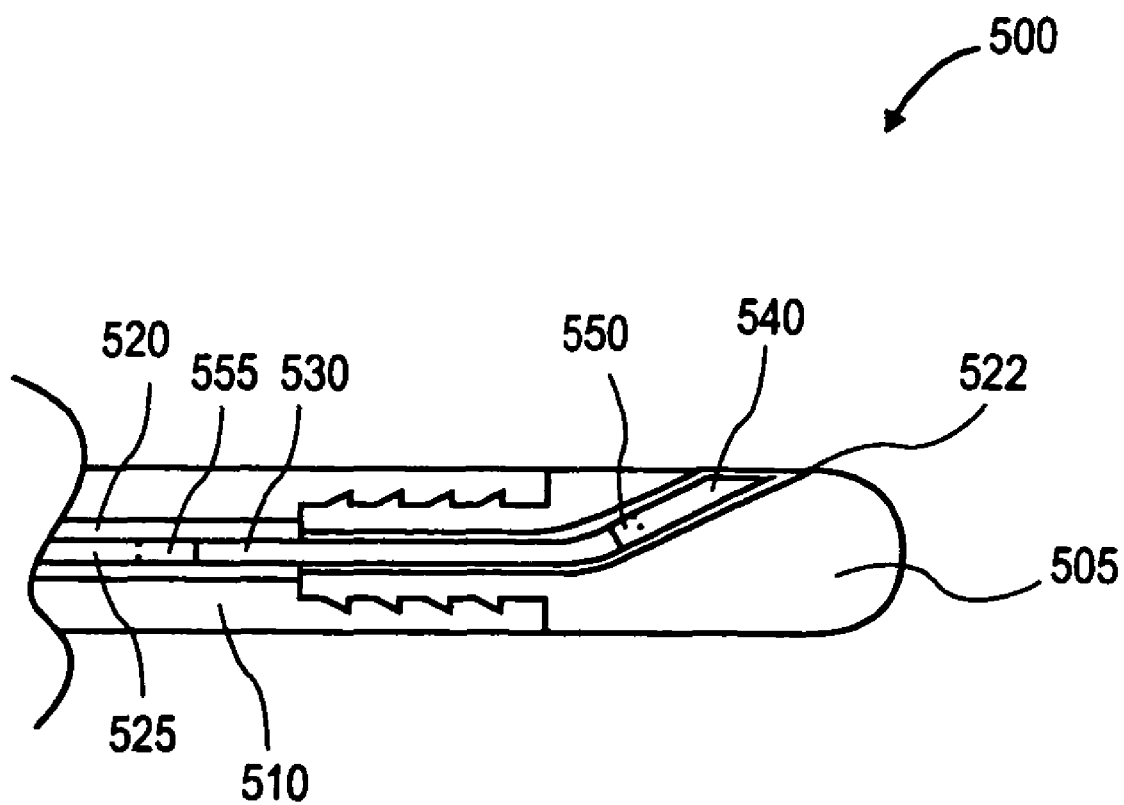
FIG. 5 illustrates an exemplary embodiment of a needle catheter.

FIG. 5 illustrates one embodiment of distal tip 505 region of needle catheter 500 having a flexible needle. Catheter body 510 encloses needle lumen 520 which extends from a proximal region (not shown) towards distal tip 505. Needle lumen 520, however, does not extend straight towards distal tip 505. Needle lumen 520 angles upwards to needle lumen opening 522. This type of configuration for needle lumen 520 may be applicable for penetrating a vessel wall after needle catheter 500 has been advanced to a target treatment region (not shown). Needle tip portion 540 is illustrated retracted within needle lumen 520. Needle tip portion is coupled to flexible polymer portion 530 at one end by a first overlap joint 550.

Flexible polymer portion is coupled to needle shaft 525 at its other end by a second overlap joint 555. First overlap joint 550 has needle tip portion 540 overlapping flexible polymer portion 530, and second overlap joint 555 has needle shaft 525 overlapping flexible polymer portion 530. In an alternative embodiment, either or both overlap may be reversed. As illustrated, flexible polymer portion 530 of the needle enables needle tip portion to bend at an angle upwards relative to the longitudinal length of catheter body 510. Needle lumen 520 serves to guide needle tip portion 540 towards opening 522 such that in an extended position, needle tip portion 540 may penetrate a body tissue. The bend of flexible polymer portion 530 is illustrative of a wide range of angles that may easily be achieved. A control handle (not shown) at the proximal end of needle catheter 500 is used to selectively extend and retract needle tip portion 540. Various depth sensors or controls may be used in this and other embodiments to sense and/or control the depth of penetration of needle tip portion 540 into the target tissue.

Figure 6:
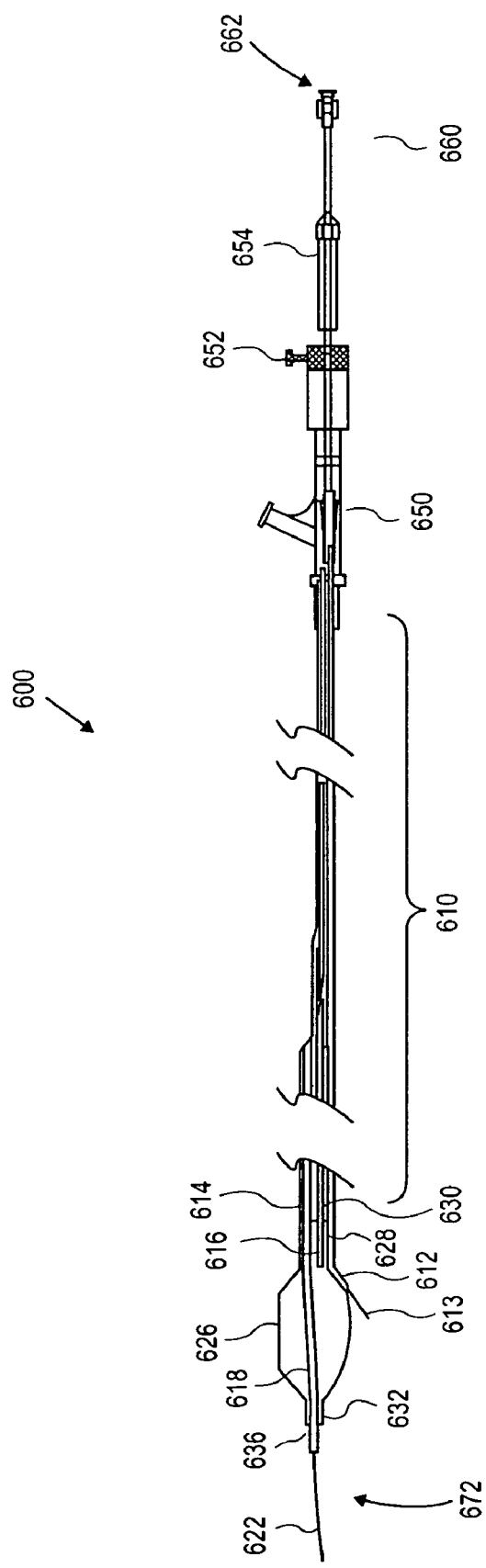
FIG. 6 illustrates another exemplary embodiment of a needle catheter.

FIG. 6 illustrates a cross sectional view of one embodiment of a needle catheter for injecting a biologic agent or therapeutic drug into a body tissue. In one embodiment, needle catheter 600 may have elongated catheter body 610 that surrounds needle lumen 612 and inner lumen 614. Housed within inner lumen 614 are fluid lumen 616 and inner member 618 that also contains guide wire 622 within guide wire lumen (not shown). Inflatable balloon 626 is coupled to inner lumen 614 and the inner member 618. Proximal end 628 of balloon 626 is coupled to distal end 630 of inner lumen 614 and distal end 632 of balloon 626 is coupled to distal end 636 of inner member 618.

In an alternative embodiment, both guide wire 622 and a retractable ultrasonic element (not shown) may be housed within inner member 614. Elongate body 610 surrounds inner member 614 and needle lumen 612. Housed within inner lumen 614 are inner member 618 and fluid lumen 616. Inner member 618 surrounds guide wire 622. Inflatable balloon 626 is coupled to inner lumen 614 and inner member 618. Proximal end 628 of balloon 626 is coupled to distal end 630 of inner lumen 614 and distal end 632 of balloon 626 is coupled to distal end 636 of inner member 618.

As further illustrated in FIG. 6, retractable needle 613 is housed in needle lumen 612 and freely movable therein. The hollow, tubular shaped needle 613 in one embodiment, may have an inner diameter within a range of approximately 0.002 inch to 0.010 inch ($5.1 \times 10^{-3}$ cm to $25.4 \times 10^{-3}$ cm) and an outer diameter within the range of approximately 0.004 inch to 0.012 inch ($10.2 \times 10^{-3}$ cm to $30.5 \times 10^{-3}$ cm). The hollow needle provides a fluid channel that extends from proximal end 662 to a distal end of needle 613. Inflatable balloon 626, illustrated in an expanded state, bends needle lumen 612 along with needle 613 at an angle away from inflatable balloon 626. In one embodiment, needle 613 may have a radius of curvature of about 30 degrees to 90 degrees. The flexibility of needle 613 facilitates placement of the needle tip near or within a desired target of a plaque or treatment region. As discussed above, needle 613 may be formed from a variety of metals including, but not limited to stainless steel, NiTi or other comparable semi-rigid and rigid materials.

Referring again to FIG. 6, a proximal end of needle 613 may be coupled to adapter 650 that couples needle 613 to needle lock 652 and needle adjustment knob 654. Needle lock 652 is used to secure needle 613 in place and prevent further movement of needle 613 within an arterial lumen once needle 613 is placed in the target position. Needle adjustment knob 654 controls accurate needle extension out of the distal end of the catheter and depth of penetration into the plaque or target treatment region. As such, movement of needle adjustment knob 654 moves needle 613 in and out of needle lumen 612. Once needle 613 has penetrated a target to a desired depth, needle lock 652 enables needle 613 to be secured in place thereby preventing any movement of needle 613 within needle lumen 612.

A drug injection port 660 may be disposed near proximal end 662 of needle catheter 600. Drug injection port 660 couples needle catheter 600 with various dispensing devices such as a syringe or fluid pump. Fluids injected into drug injection port 660 travel through needle 613 and are dispensed from the distal tip of needle 613.

Figure 7:
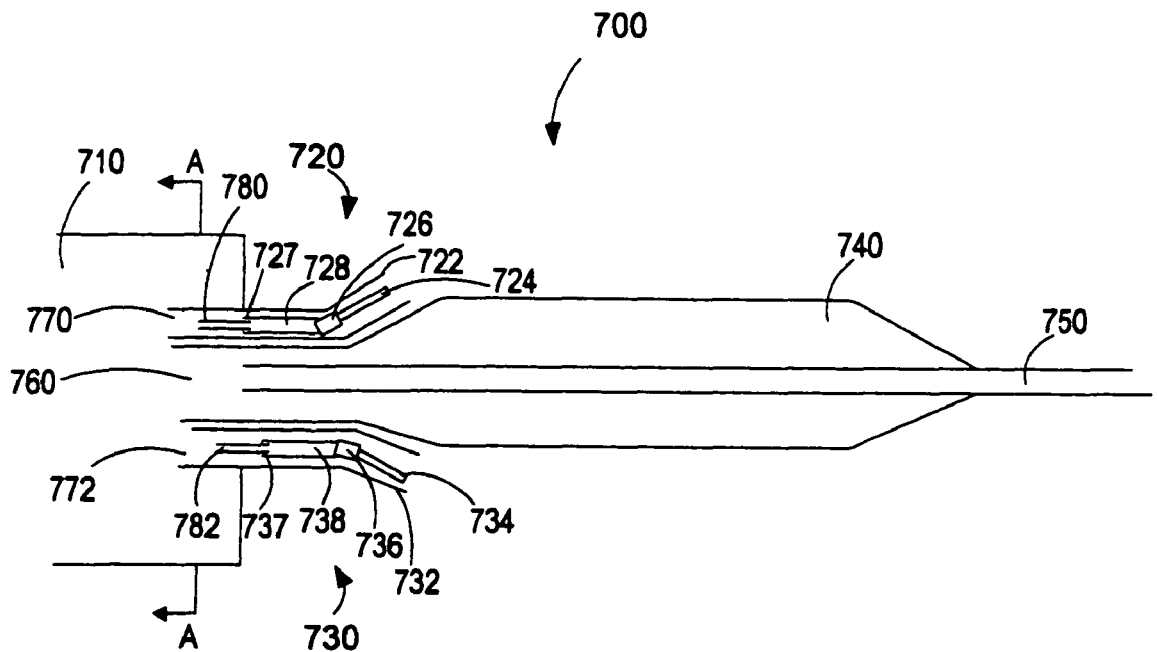
FIG. 7 illustrates another exemplary embodiment of a needle catheter.
Figure 7A:
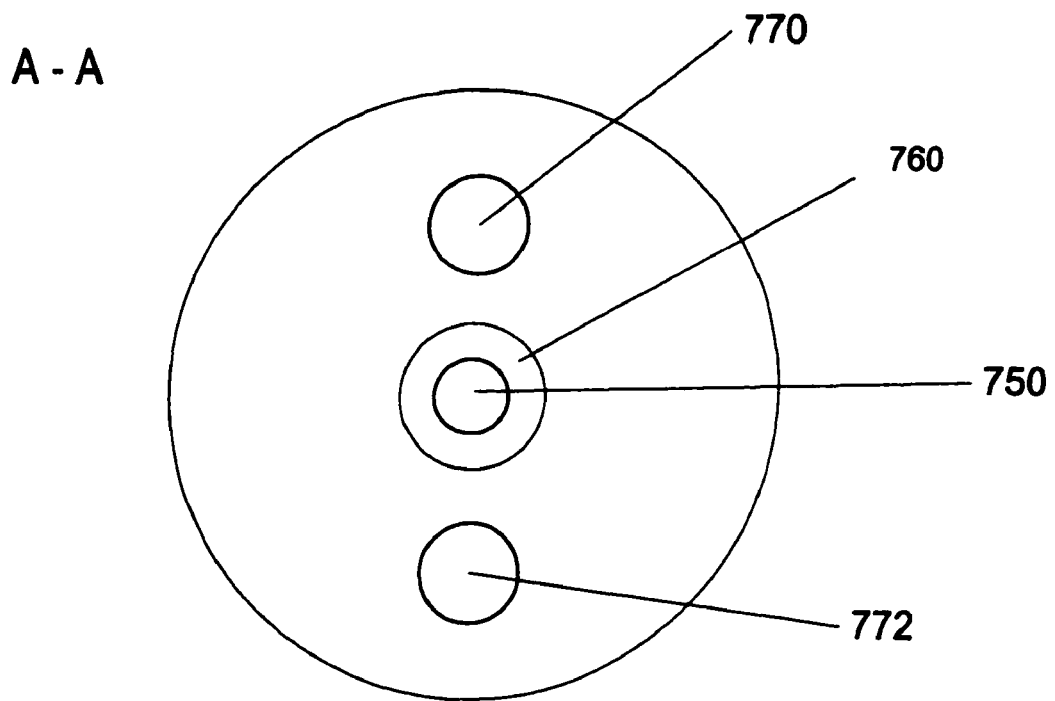
FIG. 7A illustrates a cross sectional view of the needle catheter illustrated in FIG. 7.

FIGS. 7 and 7A illustrate cross-sectional views of another embodiment of a needle catheter 700, in particular, a distal region having expandable member 740 (e.g., an angioplasty-type balloon) that may control a penetration angle of dual needle assemblies 720, 730. Dual needles may be an effective way to deliver a uniform dosage of a drug or bioactive agent to a vessel wall because in many instances, a vessel growth or occlusion may be present all along the inner wall (e.g., around the complete circumference of an arterial wall). Moreover, a dual needle catheter may reduce the number of percutaneous procedures necessary to treat a particular treatment region. The distal region of catheter 700 has an end of catheter body 710 from which expandable member 740 extends. In one embodiment, a guidewire lumen 750 (that may be formed by a tubing within catheter 700) may be present along a longitudinal length of catheter body 710 through expandable member 740. The distal end of expandable member 740 is sealed to the tubing forming guidewire lumen 750. Inflation lumen 760 also extends from catheter body 710 to expandable member.

Needle sheaths 722, 732 having lumens 770, 772 are disposed along a surface of expandable member 740 near its proximal end. Needle sheaths 722, 732 conform to the shape of expandable member 740, illustrated in its expanded or inflated state. Needle 720, having tip portion 724 coupled to flexible portion 728, is disposed within needle sheath 722. A portion of needle shaft 780, coupled to flexible portion 728, may also be disposed within needle sheath 722. Needle tip portion 724 forms a first overlapping joint 726 with flexible portion 728 and needle shaft 780 forms a second overlapping joint 727. Similarly, Needle 730, having tip portion 734 coupled to flexible portion 738, is disposed within needle sheath 732. A portion of needle shaft 782, coupled to flexible portion 738, may also be disposed within needle sheath 732. Needle tip portion 734 forms a first overlapping joint 736 with flexible portion 738 and needle shaft 782 forms a second overlapping joint 737. Needle shaft 780 and 782 extend back to and are coupled to a control handle at a proximal end of catheter 700, and the control handle allows the needles to be selectively extended and retracted.

In an alternative embodiment, second overlapping joints 727, 737 may not be present, such that flexible portion 728, 738 extend all the way to a proximal end of needle catheter 700. Additionally, as discussed above, flexible portions 728, 738 may be reinforced with braided, with a coiled wire or wires, or with combinations of coils and/or braids within its walls. Needle tip portions 724, 734 may have two positions when in use. A first retracted position, as illustrated, has needle tip portions 724, 734 completely housed within sheaths 722, 732. In this retracted position, first overlapping joints 726, 736 should be positioned distal to the bend point of needle sheath 722, 732, that is, closer to the openings of the needle sheaths. Because needle tip portions are rigid, they may most likely not bend if any part of needle tip portion traverses the bend point of needle sheaths 722, 732 as expandable member 740 increases in size (i.e., expands).

Flexible portions 728, 738 also limit the friction forces between needle tip portions 724, 734 and sheaths 722, 732, respectively, because this area may be bent to direct the needles off-axis to the catheter and into/through a vessel wall. This type of bend may be more tortuous (i.e., having a lower radius of curvature) than shafts 780, 782. Moreover, if flexible portions 728, 738 are not made more flexible than needle tip portions 724, 734, then the forces on needle sheaths 722, 732 from needle assemblies 720, 730 may cause them to separate from the catheter body and/or greatly deform at the bend point during needle assembly advancement (i.e., when expandable member 740 is inflated). If needle sheaths 722, 732 are greatly deformed or separated from these forces, then needles assemblies 720, 730 may not follow the angle dictated by the shape of expandable member 740 in its path toward a vessel wall during extension. Because the angle of needle tip portions 724, 734 to a desired target region may be less, their paths may not longer reach the same penetration depth into the vessel. This may result in the operator of needle catheter 700 no longer having control to inject needle tip portions 724, 734 to the desired target region.

A flexible needle shaft (e.g., needle shafts 780, 782) may limit the forces between the needle sheaths (or catheter) and the needle assemblies (e.g., flexible needle portion 728 and needle tip portion 724) from bending that may cause friction forces, making it difficult to control the advancement/retraction of the needle assemblies. For example, if these forces are high, the needle assembly is harder to advance and the advancement forces act as a tensile force on the catheter causing it and the sheaths to stretch, preventing the needle from extending away from the catheter body as desired or designed. The catheter may get longer but the needle assembly, in compression at the same level of force, tends to shorten, so the penetration depth is relatively less. Because the catheter gets longer, injection position control and injection depth control may be compromised. In extreme cases, the catheter may continue to stretch appreciably once the needle has engaged the wall. Then, when the advancement is completed and no more force is applied to the needle assembly (and hence to the catheter/sheaths), the catheter may spring back to its original, shorter length which may disengage the needle from the vessel wall, increase the needle's penetration depth and/or further damage the vessel wall. The needle may be made smaller, but the flow resistance increases significantly (i.e., low flow rate) making it very difficult to make injections by hand/syringe within any reasonable time frame, even with low compliance.

Referring to FIGS. 8A-8D, an exemplary method of delivering a biologic agent to a body tissue using a flexible needle catheter is illustrated. In one embodiment, needle catheter 800 may be comparable to needle catheters 600 and 700 described in detail above with respect to FIGS. 6 and 7. At FIG. 8A, a distal end 820 of needle catheter 800 is advanced through vessel lumen 805 to a target tissue region (e.g., vessel wall 810). In one embodiment, needle catheter 800 may be an over-the-wire type in which a guidewire lumen extends from a proximal end of needle catheter 800 to a distal end, enabling needle catheter 800 to advance over the guidewire to a location in vessel lumen 805 (e.g., of a patient). As an alternative to an over-the-wire catheter, a rapid exchange catheter delivery system may be utilized. As such, the catheter may be any of the catheter types used in the art, including but not limited to "rapid exchange" (RX) catheters, "over-the-wire" (OTW) catheters, or a "tip RX" catheters. To facilitate its passage through vessel lumen 805, needle catheter 800 maintains a low profile, with expandable balloon 840 in a collapsed state and needles (not shown) in a retracted position within needle sheaths 825, 830. At FIG. 8B, balloon 840 begins to expand by passing an inflation medium through an inflation lumen (e.g., inflation lumen 760 from FIGS. 7 and 7A). The inflation medium may be any type common in the art of balloon catheter technology and angioplasty balloons (e.g., fluids, including gas and liquid). As balloon 840 expands, needle sheaths 825, 830, disposed along a surface of balloon 840 near its proximal end, bends in the direction of vessel wall 810.

At FIG. 8C, balloon 840 has reached a desired inflation size such that needle sheaths 825, 830 point towards a target region of vessel wall 810 which may be a coronary artery or an artery which supplies oxygen to the brain. From here, needle tip portions 850, 855 advance past the opening of needle sheaths 825, 830 from a retracted position to an extended position to penetrate vessel wall 810. At FIG. 8D, biologically active or therapeutic agents 860, 865 are delivered from a proximal end of the catheter through needle tip portions 850, 855. Once a desired dosage of biologically active agents 860, 865 have been delivered to vessel wall 810, needle tip portions 850, 855 are retracted back into needle sheaths 825, 830, expandable balloon 840 is deflated, and the needle catheter removed back through vessel lumen 805. The advantage of utilizing a needle catheter having a flexible portion coupled to the needle tip portion is that the needle tip portions may be easily angled to a wide range of positions to target a vessel wall. The polymeric nature of the flexible portion coupled to the needle tip portion prevents kinking during both catheter advancement through a vessel lumen and penetration of a body tissue. (e.g., vessel wall). To reinforce flexible polymer portion 825, 830, braided or coiled wire may be embedded within its walls as described above.

Figure 9:
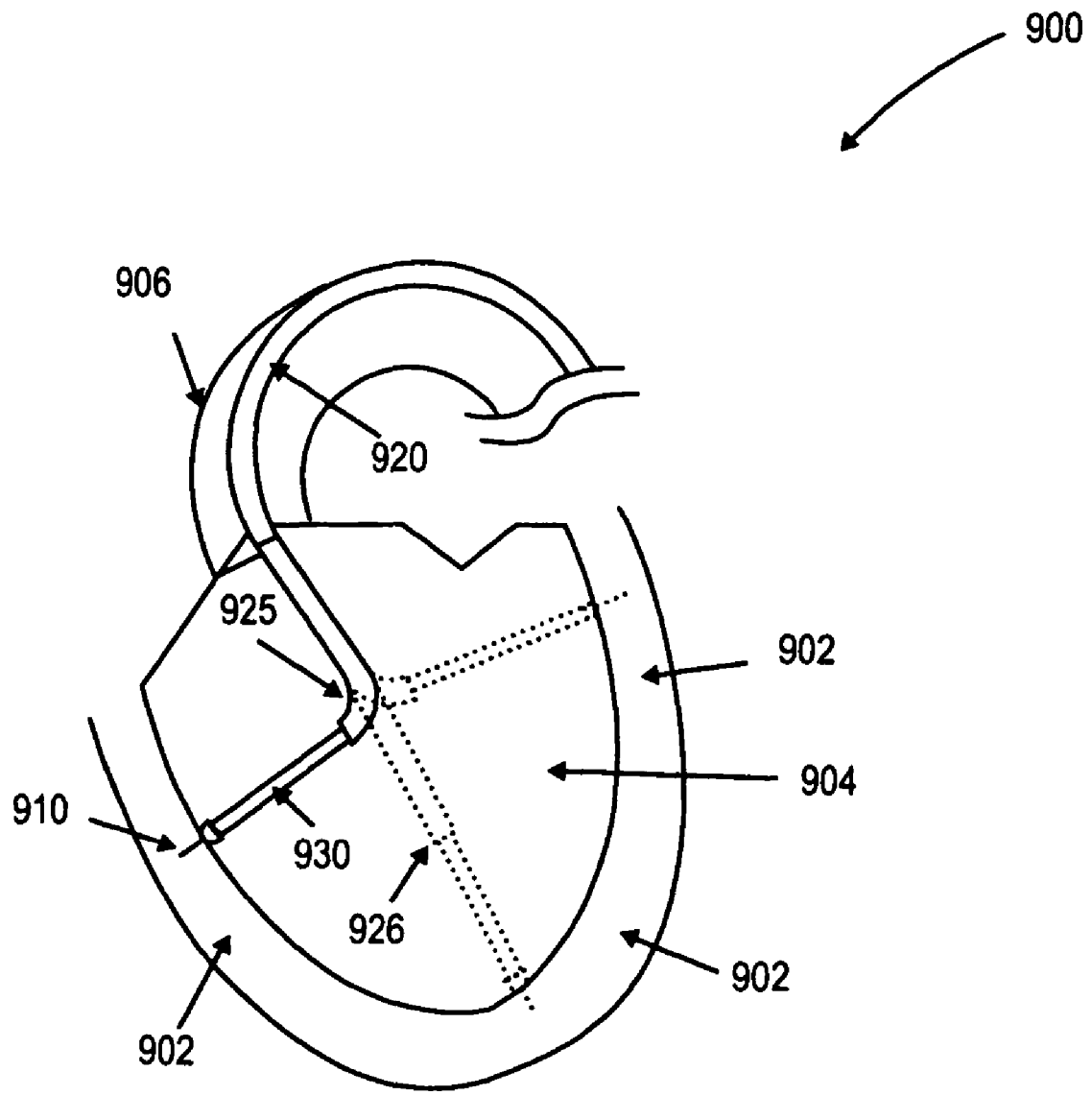
FIG. 9 illustrates an exemplary method of delivering a biologic agent to an intraventricular wall with one embodiment of a flexible needle catheter.

FIG. 9 illustrates an exemplary method of delivering a biologic agent to an intraventricular wall of the heart with one embodiment of a flexible needle catheter assembly 900 of the present invention. Needle 910 is shown in its distal most, extended position and penetrating myocardium 902. The distal end of the modified guiding catheter 920 is shown resident in left ventricle 904 and aorta 906, although it may be appreciated that other insertion sites for the needle catheter may be chosen to access the other chambers of the heart, if desired. At an extreme distal end of guide 920 is articulating section 925, which can be deflected into a number of curved positions. Guiding catheter's 920 ID and needle catheter 930 OD may be chosen such that needle catheter 930 is extendable out of guiding catheter 920. The curve of articulating section 925 directs needle catheter 930 toward the desired area of myocardium 902. Dotted line structure 926 is a representation of articulating section 925 and needle catheter 930 in a relatively straight position. By advancing or retracting guide catheter 920 and adjusting the curvature of its articulating section 925, retracted needle catheter 930 may be advanced into contact with all areas of the myocardium 902 along a line up the left side of ventricle 904, such that needle 910 may penetrate myocardium 902 at a high angle (in the vicinity of 60°-90°) to ensure an adequate depth of penetration. By rotating guide catheter 920, this line may be swept such that all areas of myocardium 902 within ventricle 904 may be accessed in this manner. In one embodiment, distal end of guide 920 and needle catheter 930 be radiopaque, such that they may be observed under fluoroscopy. In another embodiment, guide 920 may be made 8 F or smaller and still accommodate needle shaft 930.

For the type of use described with respect to FIG. 9 (i.e., intra-cardiac drug delivery), size constraints for needle catheter 900 may not be as severe compared to a needle catheter used for drug delivery within a tortuous vessel lumen. As such, needle shaft dimensions may be chosen to be larger (OD/ID/wall thickness), but high flexibility may still be desired to facilitate guide insertion and/or placement and guide tip deflection. High flexibility may also be desired to limit the contact pressure of needle catheter 930 against the cardiac wall, to prevent trauma, arrhythmia, or both. A larger ID for needle catheter 930 causes the flow resistance to be reduced dramatically in needle catheter 930, so compliance issues may be mitigated. A full length, polymer shaft (as opposed to a metallic shaft or combination polymer/metallic shaft) may be more practical, in which case the needle shaft may contain a braid(s) and/or spring(s) to improve compression, burst strength and compliance properties. Polymer blends that may be adhered to the braid(s) and/or spring(s) include for example, PRIMACOR copolymers.

As noted above, compliance may be an issue in high flow resistance tubes (e.g., needle catheter 700 of FIG. 7). Compliance is the change in lumen volume per unit change in lumen pressure. As the flow resistance increases, the pressure is proportionally higher at any point in the lumen at any give flow rate. Thus, during injection by an operator in high flow resistance tubes and/or high compliance tubes, part of the injected material volume fills the increasing volume of the lumen (i.e., injectate is stored by the expanding lumen). After injection, the pressure begins to drop and the lumen begins to return to its normal volume, slowly squeezing out the rest of the injected material against the flow resistance of the needle assembly. Thus, even though the operator may have injected the material very rapidly into the proximal end of the needle catheter, the material may flow very slowly out of the distal end of the needle assembly for an extended period of time with an increasing and then decreasing flowrate. The actual injection time can become relatively long and be very different from that perceived by an operator. This may result in long treatment times and/or the premature retraction of the needle assembly prior to the proper dose being delivered.

If the flow resistance is low, then the pressure in the lumen may be low and very little injectate is stored during injection and, after injection, the stored injectate is rapidly expelled because the low flow resistance enables it to leave rapidly (or the stored injectate volume become negligible). If the compliance is low, then little injectate is stored in the lumen, regardless of the pressure, and it may take very little time to expel the injectate, regardless of the flow resistance.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A catheter, comprising:
   an elongated tubular member having a proximal end and a distal end; and
   an expandable member having a shoulder region disposed near the distal end of the elongated tubular member;
   a needle disposed in a needle lumen over the shoulder region of the expandable member near the distal end, the needle comprising a rigid, penetrating tip coupled to a flexible portion by an overlapping joint, wherein the flexible portion enables the needle to bend to a penetrating angle controlled by an angle of the shoulder region relative to the distal end of the elongated tubular member upon expansion of the expandable member and penetrate a body tissue without kinking,
   wherein the needle is movable within the needle lumen.

2. The catheter of claim 1, further comprising a flexible needle sheath that is coupled adjacent to the shoulder region of the expandable member disposed over the needle, wherein the needle remains within the needle sheath in a retracted position, and extends out of the needle sheath in a penetrating position.

3. The catheter of claim 1, wherein the overlapping joint has the rigid, penetrating tip disposed over the flexible portion.

4. The catheter of claim 1, wherein the overlapping joint has the flexible portion disposed over the rigid, penetrating tip.

5. The catheter of claim 1, wherein the flexible portion that forms the overlapping joint with the rigid, penetrating tip is reinforced with a metallic material disposed within the flexible portion.

6. The catheter of claim 5, wherein the metallic material forms a wire mesh within the flexible portion.

7. The catheter of claim 5, wherein the metallic material forms a coil within the flexible portion.

8. The catheter of claim 1, wherein the rigid, penetrating tip is made from stainless steel.

9. The catheter of claim 1, wherein the rigid, penetrating tip is made from nickel-titanium (NiTi).

10. The catheter of claim 1, wherein the rigid, penetrating tip is made from a ceramic material.

11. The catheter of claim 1, wherein the flexible portion is selected from a group consisting of polyimide, polyether block amide or polyester block amide (PEBAX), polyetheretherketone (PEEK), polyethylene terephthalate (PET), polybutylene terephthalate (PBT), polyetherimide (PEI), polystyrene (PS), acetel, polymethylmethacrylate (PMMA or acrylic), nylon, Teflon, and polyvinyl chloride (PVC).

12. A catheter, comprising:
an elongated tubular member;
a needle shaft disposed within a lumen of the elongated tubular member, the needle shaft having a proximal portion and a distal portion;
an expandable member having a shoulder region disposed near the distal portion of the needle shaft; and
a needle coupled to the distal portion of the needle shaft, the needle positioned adjacent and over the shoulder region of the expandable member, the needle comprising a polymeric tube portion coupled to a rigid tip portion by a first overlapping joint, wherein the polymeric tube portion enables the needle to bend to a penetration angle determined by an angle of the shoulder region upon expansion of the expandable member and penetrate a body tissue without kinking.

13. The catheter of claim 12, further comprising a needle sheath to house the needle, when the needle is in a retracted position.

14. The catheter of claim 12, wherein the needle shaft comprises a metallic material, wherein the distal portion of the needle shaft is coupled to the polymeric tube portion by a second overlapping joint.

15. The catheter of claim 12, wherein the needle shaft comprises a polymeric material, wherein the distal portion of the needle shaft is coupled to the polymeric tube portion by a second overlapping joint.

16. The catheter of claim 12, wherein the first overlapping joint has the rigid, tip portion disposed over the polymeric tube portion.

17. The catheter of claim 12, wherein the first overlapping joint has the polymeric tube portion disposed over the rigid, tip portion.

18. The catheter of claim 12, wherein the polymeric tube portion that forms the first overlapping joint with the rigid, tip portion is reinforced with a metallic material disposed within the polymeric tube portion.

19. The catheter of claim 18, wherein the metallic material forms a wire mesh within the polymeric tube portion.

20. The catheter of claim 18, wherein the metallic material forms a coil within the polymeric tube portion.

21. The catheter of claim 12, wherein the rigid, tip portion is made from stainless steel.

22. The catheter of claim 12, wherein the rigid, tip portion is made from nickel-titanium (NiTi).

23. The catheter of claim 12, wherein the rigid, tip portion is made from a ceramic material.

24. The catheter of claim 12, wherein the polymeric tube portion is selected from a group consisting of: polyimide, polyether block amide or polyester block amide (PEBAX), polyetherketone (PEEK), polyethylene terephthalate (PET), polybutylene terephthalate (PBT), polyetherimide (PEI), polystyrene (PS), acetel, polymethylmethacrylate (PMMA or acrylic), nylon, Teflon, and polyvinyl chloride (PVC).

25. A catheter of claim 12, wherein the expandable member comprises a balloon.

26. The catheter of claim 12, wherein the needle shaft has a lumen to deliver a biologic agent through the needle.

27. A catheter, comprising:
an elongated tubular member having a proximal end and a distal end; and
an expandable member having a shoulder region disposed near the distal end of the elongated tubular member;
a needle disposed in a needle lumen near the distal end, the needle comprising a rigid, penetrating tip coupled to a flexible portion the needle being movable within the needle lumen; and
means for bending the needle to a penetration angle, wherein the flexible portion enables the needle to bend to the penetration angle controlled by an angle of the shoulder region relative to the distal end of the elongated tubular member upon expansion of the expandable member and penetrate a body tissue without kinking.

28. The catheter of claim 27, further comprising:
a needle shaft coupled to the flexible portion; and
means for bending a second needle to a second penetration angle.

29. The catheter of claim 27, further comprising means for reinforcing the flexible portion with a braided wire.

30. The catheter of claim 27, further comprising means for reinforcing the flexible portion with a coiled spring.

* * * * *